United States Patent [19]

Van Haften et al.

[11] Patent Number: 5,328,889

[45] Date of Patent: *Jul. 12, 1994

[54] DRY, WATER-SOLUBLE, SUBSTITUTED PHENOXY AND/OR BENZOIC ACID HERBICIDES AND METHOD OF PREPARING SAME

[75] Inventors: John L. Van Haften, Leawood; Roger P. Cahoy, Overland Park, both of Kans.

[73] Assignee: PBI-Gordon Corporation, Kansas City, Mo.

[*] Notice: The portion of the term of this patent subsequent to Aug. 16, 2008 has been disclaimed.

[21] Appl. No.: 928,132

[22] Filed: Aug. 10, 1992

Related U.S. Application Data

[63] Continuation-in-part of Ser. No. 911,757, Jul. 10, 1992, abandoned.

[51] Int. Cl.$^5$ .................. A01N 25/12; A01N 33/06; A01N 37/38; A01N 37/40
[52] U.S. Cl. .................. 504/116; 504/144; 504/145; 504/322; 504/323; 504/324; 71/DIG. 1
[58] Field of Search .............. 504/323, 324, 116, 322, 504/144, 145; 71/DIG. 1

[56] References Cited

U.S. PATENT DOCUMENTS

| | | | |
|---|---|---|---|
| 4,015,970 | 4/1977 | Hennart | 71/11 |
| 4,332,614 | 6/1982 | Alt | 71/118 |
| 5,022,182 | 6/1991 | Anderson | 47/48.5 |
| 5,022,917 | 6/1991 | Graham | 71/93 |

OTHER PUBLICATIONS

The Chemistry of Open-Chain Organic Nitrogen Compounds, vol. I, P. A. S. Smith, pp. 267-269 (1965).
Advances in Pesticide Formulation Technology, ACS Symposium Series 254, Paper 14, "Steps of Water Dispersible Granule Development", Wright and Ibrahim, pp. 185-192 (1984).
Pesticide Formulations, Innovations and Developments, ACS Symposium Series 371, Chapter 20, "Development of Solid Pesticide Formulations by Fluidized-Bed Technology", Lin, pp. 251-259 (1988).

Primary Examiner—Richard L. Raymond
Assistant Examiner—S. Mark Clardy
Attorney, Agent, or Firm—Hovey, Williams, Timmons & Collins

[57] ABSTRACT

A dry, water-soluble, substituted phenoxy and/or benzoic acid herbicide is prepared by grinding and dry blending the herbicide in acid form with anhydrous trisodium phosphate or tripotassium phosphate which functions as a solid solubilization medium. At least about 0.6 mole of the medium is provided for each mole of active herbicidal agent in the initially dry blended mixture.

20 Claims, No Drawings

DRY, WATER-SOLUBLE, SUBSTITUTED PHENOXY AND/OR BENZOIC ACID HERBICIDES AND METHOD OF PREPARING SAME

RELATED APPLICATION

This application is a continuation-in-part of application Ser. No. 07/911,757, filed Jul 10, 1992, of the same title, and now abandoned.

BACKGROUND OF THE INVENTION

1 Field of the Invention

This invention relates to water-soluble herbicidal compositions in dry powdered form which include herbicidally active substituted phenoxy and/or benzoic acids that alone are not readily soluble in water.

2. Description of the Prior Art

Those herbicidal agents registered for use by commercial applicators are generally sold in concentrated form for economy of transport, and then diluted by the applicator either at a central distribution center, or less frequently at the point of use. The majority of effective herbicides and plant growth regulators are foliarly absorbed and therefore, to be effective, must be applied to the foliage of the target pest species. Other herbicides are root absorbed and the product must be applied in a manner as to be available to the roots of the target. This is commonly accomplished by spraying a dilute water solution, or dispersion of the desired pesticide on the vegetation to be treated. Most herbicides are therefore marketed as either (1) liquid or dry water-soluble formulations, (2) liquid, water emulsifiable formulations, or (3) solid or liquid water dispersible formulations. The concentrated formulations are diluted to the required effective concentration by the person doing the spray application. Thus, in order to obtain optimum effectiveness and to minimize agitation and other mechanical suspension requirements, water-soluble formulations are normally preferred.

Because of the difficulties of manufacturing a dry, soluble form of herbicide, most dry formulations are simply dispersible forms of essentially insoluble active ingredients. Typical examples of formulations are (1) wettable powders, (2) water dispersible granules, or (3) dry flowables. Formulations of these types depend heavily on surfactants and grinding techniques to provide a dry formulation of active ingredients that can be temporarily dispersed or suspended in water for spray application. Even when a dispersion can initially be obtained in water, the time of full dispersion is usually limited, thus requiring stirring, agitation with air, or other mechanical mixing. Dispersions of this type present additional problems in that the material tends to clog spray nozzles and other distribution components, and require the user to prepare smaller than desired batches in order to minimize application problems.

Because of the problems associated with attempting to prepare the dry powdered herbicide, suppliers have resorted in some instances to dissolution of the active ingredient in an organic solvent such as mineral spirits or the like. The concentrated formulation, containing suitable surfactants, is then diluted with water to form a dispersion that again usually necessitates some type of agitation to maintain the phases substantially homogeneous for a useful period of time.

In instances where the herbicides are dissolved in a solvent for shipment as a concentrate, the solvent presents health and physical hazards to the manufacturer as well as the user, the solvents add to the overall cost of the product, and the solvent agent is oftentimes phytotoxic to desirable plant species.

The wettable powders and solvent dissolved herbicides are frequently packaged in plastic containers and disposal of these plastic packages is becoming increasingly difficult from an environmental standpoint.

Substituted phenoxy and/or benzoic acid herbicides such as (2,4-dichlorophenoxy)acetic acid (2,4-D), 4-(2,4-dichlorophenoxy) butanoic acid (2,4-DB), ($\pm$)-2-(4-chloro-2-methylphenoxy) propanoic acid (MCPP), (4-chloro-2-methylphenoxy)acetic acid (MCPA), (35)-2-(2,4-dichlorophenoxy)propanoic acid (dichloroporp), 3,6-dichloro-2-methoxybenzoic acid (dicamba), and 3-amino2,5-dichlorobenzoic acid (chloramben) have long been used to control unwanted vegetation.

These substituted phenoxy and/or benzoic acid herbicides are white crystalline solids with very low vapor pressures and low water solubilities. They are soluble only in alkaline solutions or polar organic solvents.

Phenoxy and/or benzoic acid herbicides are available commercially as acid, ester, alkali metal, and amine salt formulations that can also be applied as mixtures with other herbicides. The alkali metal and especially the amine salt formulations are preferred because they are the most water-soluble and can be more readily applied as aqueous sprays. However, the esters must be applied either as emulsions in water, or as solutions in organic solvents such as oils. 2,4-D for example, is an insoluble crystalline material having a $pK_a$ of approximately 2.6. For ease of application, 2,4-D is normally converted to a water-soluble amine or mineral salt by the manufacturer and then dissolved by the applicator in a water carrier before use.

However, water-soluble substituted phenoxy and/or benzoic acid salts exhibiting herbicidal activity are difficult to prepare in a dry state. Soluble salts such as potassium or sodium or dimethylamine must be first prepared in water or a solvent and then the solvent removed. This requires special equipment, is energy intensive, and frequently generates undesirable waste products. As a consequence, most dry forms of herbicide that are marketed are not of a soluble type but rather are merely dispersible forms of the essentially insoluble herbicide acid which are distributed as a wettable powder or a wettable, dispersible granule. Although both inorganic and organic salt forms are commercially available, the most common salt form is the dimethylamine salt of the substituted phenoxy or substituted benzoic acid herbicide. Typical formulations range from about 20% to 50% active ingredient concentrations in water or solvent solutions.

SUMMARY OF THE INVENTION

The present invention relates to a method of preparing dry, water-soluble, substituted phenoxy and/or benzoic acid herbicides which are in acid form. The invention also concerns dry phenoxy and/or benzoic acid herbicidal powders which may be dissolved in water at concentrations providing from at least about 0.1% to at least about 2-1/2% by weight of the active herbicide in the final herbicidal solution.

A dry herbicidal product is preferred over a liquid concentrated herbicide for a number of reasons. Dry formulations are more stable to temperature variations encountered in storage and shipping. For example, freezing can destabilize liquid products interfering with the effectiveness of the herbicide. Similarly, high storage temperatures can lead to solvent losses when an organic solvent is used to dissolve the agent or cause hydrolysis when water is a solvent, thereby adversely affecting active ingredient concentrations.

Dry herbicidal formulations are less dangerous than liquid products. Package leakage during handling is much less likely. If accidentally punctured, dry package leakage is much less severe and easier to clean up than a liquid product. Also, personnel protection is easier to accomplish with dry products because the material cannot as easily splash into the eyes or skin of the applicator. Spills of solvent containing formulations are potentially flammable, further militating against the use of solvents for dissolving the herbicide.

The ease of packaging is significantly enhanced with dry products over liquid formulations and packaging flexibilities are greatly enhanced. Paper containers or wax treated packages can be used, as well as plastic containers. With liquids, specially treated plastic containers or glass containers are normally required. Paper or cardboard packages can be compressed and disposed of much easier than plastic, glass or metal containers.

Transportation costs of dry products are potentially less expensive than is the case where a liquid carrier must also be transported. Although a number of concentrated liquid products having a fairly high active ingredient content are in commercial use, many formulations are sold in the 20-30% active ingredient range with the remainder of the product being water along with a small amount of dispersing agents or product appearance or handling enhancers.

The dry, water-soluble, substituted phenoxy and/or benzoic acid herbicides of the subject invention are prepared by dry blending the herbicidal agent with a quantity of solid, substantially anhydrous, trisodium phosphate (TSP) or anhydrous tripotassium phosphate (TPP) which serves as a solubilization medium for the herbicidal agent. A sufficient amount of the TSP or TPP solubilization medium provided in the dry blended mixture in relationship to the quantity of herbicidal agent combined therewith to cause the dry blended mixture to substantially dissolve in water during preparation of a herbicidal solution which contains an adequate proportion of the herbicidal agent to provide from about 0.1% to about 2-½% by weight of the active herbicide in the herbicidal solution.

A sufficient amount of the TSP or TPP solubilization medium is dry blended with the dry substituted phenoxy and/or benzoic acid herbicidal agent to provide at least about 0.6 mole and to about 1.15 moles of the phosphate medium for each mole of active herbicidal agent in the dry blended mixture.

The water-soluble substituted phenoxy and/or benzoic acid herbicides are easily manufactured by dry blending the ingredients in powdered form. No unusual manufacturing techniques are required such as grinding to very fine sizes or classification procedures normally necessary to obtain a suitable dispersible product. Product raw material costs are comparable to widely used organic amine phenoxy and/or benzoic acid herbicide formulations currently being marketed. The raw materials are all commercially available and readily obtainable at competitive prices. In addition to the active herbicidal ingredients, the dry blended water-soluble substituted phenoxy and/or benzoic acid herbicide contains phosphorous which functions as a potentially useful nutrient for the non-herbicidally susceptible species.

A quantity of a substantially solid herbicidal agent selected from the group consisting of substituted herbicidally active phenoxy acids and substituted herbicidally active benzoic acids, which are not readily soluble in water is added to an amount of a substantially solid solubilization medium for the herbicidal agent. The preferred solubilization agent is trisodium phosphate (TSP) or tripotassium phosphate (TPP). Examples of useful phenoxy and/or benzoic acid herbicides are (2,4-dichlorophenoxy) acetate acid (2,4-D), 4-(2,4-dichlorophenoxy)-butanoic acid (2,4-DB), (±)2-(4-chloro-2-methylphenoxy) propanoic acid (MCPP), (4-chloro-2-methylphenoxy)-acetic acid (MCPA), (±)-2-(2,4-dichlorophenoxy)propanoic acid (dichloroprop), 3,6-dichloro-2-methoxybenzoic acid (dicamba), and 3-amino-2,5-dichlorobenzoic acid (chloramben). The phenoxy and/or benzoic acid herbicides may be used alone or as combinations thereof. Preferred formulations include at least about 50 weight percent of the active herbicidal acid or combinations thereof, and in certain instances about 60 weight percent of the active herbicidal agent.

The herbicidal agent and the phosphate solubilization medium are dry blended to produce a substantially homogeneous mixture thereof. This dry blended mixture may be packaged in paper containers, or other suitable packages, without further processing such as pulverization, extended grinding, or critical classification. However, the particle size is preferably small enough to permit relatively rapid wetting when added to water. At least about 0.6 mole to about 1.15 moles of the solubilization medium is provided for each mole of active herbicidal agent in the dry blended mixture.

| Ingredients | % Active Ingredients | Weight % Reagents | Makeup for Grinding of 20 Grams - In Grams | HLPC (High Performance Liquid Chromatography Analysis) |
|---|---|---|---|---|
| 1. 2,4-D Acid - Tech. Grade-(96%) | 31.16 | 32.46 | 6.49 | 30.94 |
| 2. MCPP Acid - Tech. Grade (Dry, 95%) | 15.70 | 16.53 | 3.31 | 15.61 |
| 3. Dicamba - Tech. Grade - (86%) | 3.14 | 3.65 | 0.73 | 3.18 |
| 4. Sodium naphthalenesulfonate formaldehyde polymer (Lomar PW - Henkel) | | 1.00 | 0.20 | |
| 5. Sorbitan tristearate (SPAN -65 - ICI) | | 1.00 | 0.20 | |
| 6. Spray dry synthetic silica (Wessalon 50-S - N.A. Silica Co.) | | 5.00 | 1.00 | |
| 7. Trisodium phosphate (Anhyd) | | 40.36 | 8.07 | |
| TOTALS | | 100.00% | 20.00 gms. | |

EXAMPLE 1

| Ingredients | % Active Ingredients | Weight % Reagents | Makeup for Grinding of 20 Grams - In Grams | HLPC (High Performance Liquid Chromatography Analysis) |
|---|---|---|---|---|
| 1. 2,4-D Acid - Tech. Grade-(96%) | 31.16 | 32.46 | 6.49 | 30.94 |
| 2. MCPP Acid - Tech. Grade (Dry, 95%) | 15.70 | 16.53 | 3.31 | 15.61 |
| 3. Dicamba - Tech. Grade - (86%) | 3.14 | 3.65 | 0.73 | 3.18 |
| 4. Sodium naphthalenesulfonate formaldehyde polymer (Lomar PW - Henkel) | | 1.00 | 0.20 | |
| 5. Sorbitan tristearate (SPAN -65 - ICI) | | 1.00 | 0.20 | |
| 6. Spray dry synthetic silica (Wessalon 50-S - N.A. Silica Co.) | | 5.00 | 1.00 | |
| 7. Trisodium phosphate (Anhyd) | | 40.36 | 8.07 | |
| TOTALS | | 100.00% | 20.00 gms. | |

Ingredients 1-7 of Example 1 were ground to a fine, dry powder (averaging about 50 microns particle size) in a laboratory analytical mill. The mixture was transferred to a capped glass container. A 2 gm. sample of the 50% active herbicide powder prepared in accordance with Example 1 was added to a glass graduated cylinder which contained 98 ml. of city water. The stoppered cylinder was inverted several times over a period of 5 minutes. The 2 weight percent of herbicidal agent added to the water dissolved, with only a small quantity silica remaining as a dispersion. After 96 hours in an oven at 50° C., a sample of the powder indicated no visible changes.

EXAMPLE 2

The following ingredients were dry blended:

| Ingredients | % Active Ingredients | Weight % Reagents | Makeup for Grinding of 20 Grams - In Grams | HLPC (High Performance Liquid Chromatography Analysis) |
|---|---|---|---|---|
| 1. 2,4-D Acid - Tech. Grade-(97%) | 36.63 | 37.76 | 7.55 | 37.42 |
| 2. MCPP Acid - Tech. Grade (Dry, 95%) | 19.48 | 20.51 | 4.10 | 18.87 |
| 3. Dicamba - Tech. Grade - (86%) | 3.89 | 4.52 | 0.90 | 3.65 |
| 4. Sodium naphthalenesulfonate formaldehyde polymer (Lomar PW) | | 1.00 | 0.20 | |
| 5. Sorbitan tristearate (SPAN-65) | | 1.00 | 0.20 | |
| 6. Spray dry synthetic silica (Wessalon 50-S) | | 5.00 | 1.00 | |
| 7. Trisodium phosphate (Anhyd) | | 30.21 | 6.05 | |
| TOTALS | | 100.00% | 20.00 gms. | |

Ingredients 1-7 of Example 2 were ground to a fine, dry powder (averaging about 50 microns particle size) in a laboratory analytical mill. The mixture was transferred to a capped glass container. A 2 gm. sample of the 60% active herbicide powder prepared in accordance with Example 2 was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C. a sample of the powder indicated no visible changes.

EXAMPLE 3

The following ingredients were dry blended:

| Ingredients | % Active Ingredients | Weight % Reagents | Makeup for Grinding of 20 Grams - In Grams | HLPC (High Performance Liquid Chromatography Analysis) |
|---|---|---|---|---|
| 1. 2,4-D Acid - Tech. Grade-(97%) | 31.16 | 32.46 | 6.49 | 32.45 |
| 2. MCPP Acid - Tech. Grade (Dry, 95%) | 15.70 | 16.53 | 3.31 | 15.39 |
| 3. Dicamba - Tech. Grade - (86%) | 3.14 | 3.65 | 0.73 | 3.27 |
| 4. Sodium naphthalenesulfonate formaldehyde polymer (Lomar PW) | | 1.00 | 0.20 | |
| 5. Sorbitan tristearate (SPAN-65) | | 1.00 | 0.20 | |
| 6. Spray dry synthetic silica (Wessalon 50-S) | | 5.00 | 1.00 | |
| 7. Tripotassium phosphate (Anhyd) | | 40.36 | 8.07 | |
| TOTALS | | 100.00% | 20.00 gms. | |

Ingredients 1-7 of Example 3 were ground to a fine, dry powder (averaging about 50 microns particle size) in a laboratory analytical mill. The mixture was transferred to a capped glass container. A 2 gm. sample of the 50% active herbicide powder prepared in accordance with Example 3 was added to a glass graduated cylinder which contained 98 ml. of city water. The stoppered cylinder was inverted several times over a period of 5 minutes. The 2 weight percent of herbicidal agent added to the water dissolved, with only a small quantity of silica remaining as a dispersion. After 96 hours in an oven at 50° C., a sample of the powder indicated no visible changes.

The prepared aqueous sample containing 2.0 weight percent of the 50% or 60% active herbicide powder in all instances yielded a substantially clear solution within two minutes. It was not necessary to heat or agitate the product to maintain the ingredients in solution while sitting on a shelf for several days at room temperature. Tests of the dry blended material dissolved in water yielded clear solutions at levels of 0.5%, 1%, 2%, and 4 weight percent. Cloudiness started to appear at a level above about 5 weight percent, and 10 weight percent samples were found to be at least partially insoluble. Weight percent in this respect means 1 gram of the active dry powder for each 99 milliliters of tap water. Normal herbicide application concentrations range from about ½ weight percent of the active acid to about 2% of the active acid.

It has been determined that the best results are obtained when an anhydrous TSP or TPP is utilized as the solubilization medium for the substituted phenoxy and/or benzoic acid herbicidal agent. The preferred anhydrous TSP or TPP solubilization medium contains less than 1% water by weight.

On a parts by weight basis, the preferred dry, water-soluble substituted phenoxy and/or benzoic acid herbicide powder composition (50% by weight active ingredient) consists essentially of, on an approximately 100% active ingredient basis, about 31 parts of dry, solid powder particles of 2,4-D about 16 parts of dry, solid powder particles of MCPP, about 3 parts of dry, solid powder particles of dicamba, and about 40 parts of anhydrous TSP or anhydrous TPP.

In the case of 60 weight percent active ingredients, the preferred herbicidal powder composition consists essentially of, on an approximately 100% active ingredient basis, about 37 parts of dry, solid powder particles of 2,4-D, about 20 parts of dry, solid powder particles of MCPP, about 4 parts of dry, solid powder particles of dicamba, and about 30 parts of anhydrous TSP.

We claim:

1. A dry, water-soluble substituted phenoxy and/or benzoic acid herbicide powder composition consisting essentially of:
    a dry blended admixture of
        a first quantity of dry, powder particles of a substantially solid herbicidal agent selected from the group consisting of substituted herbicidally active phenoxy acids and substituted herbicidally active benzoic acids, which alone are not readily soluble in water, and
        a second quantity of dry, solid, powder particles selected from the group consisting of trisodium phosphate and tripotassium phosphate as a solubilization medium for the herbicidal agent,
    said first and second quantities of the herbicidal agent and the solubilization medium being the predominate constituents of the composition,
    there being from about 0.6 mole to about 1.15 mole of solubilization medium for each mole of herbicidal agent,
    said herbicidal agent and the solubilization medium having been dry blended in powdered form without changing the physical state of the particles to retain the discrete particulate character of each of said first and second quantities of said particles, and in the absence of chemical reaction between said herbicidal agent and said solubilization medium to form a relatively uniform dry mixture thereof,
    there being a sufficient quantity of the phosphate medium in the dry blended mixture in relationship to the quantity of herbicidal agent combined therewith such that the dry blended powder mixture will dissolve in water during preparation of a herbicidal solution therefrom that contains an adequate proportion of the herbicidal agent to provide from about 0.1 to about 2½% by weight of the active herbicidal agent in the herbicidal solution.

2. An herbicide as set forth in claim 1 wherein said dry solubilization medium is trisodium phosphate.

3. An herbicide as set forth in claim 1 wherein said dry solubilization medium is tripotassium phosphate.

4. An herbicide as set forth in claim 1 wherein the dry blended admixture includes a mixture of substituted phenoxy acid and substituted benzoic acid herbicides.

5. An herbicide as set forth in claim 1 wherein said active substituted phenoxy acid herbicidal agent is 2,4-dichlorophenoxy acetic acid.

6. An herbicide as set forth in claim 1 wherein said active substituted phenoxy acid herbicidal agent is 4-(2,4-dichlorophenoxy)butanoic acid.

7. An herbicide as set forth in claim 1 wherein said active substituted phenoxy acid herbicidal agent is (±)-2-(4-chloro-2-methylphenoxy)propanoic acid.

8. An herbicide as set forth in claim 1 wherein said active substituted phenoxy acid herbicidal agent is (4-chloro-2-methylphenoxy) acetic acid.

9. An herbicide as set forth in claim 1 wherein said active substituted phenoxy acid herbicidal agent is (±)-2-(2,4-dichlorophenoxy)propanoic acid.

10. An herbicide as set forth in claim 1 wherein said active substituted benzoic acid herbicidal agent is 3 6-dichloro-2-methoxybenzoic acid.

11. An herbicide as set forth in claim 1 wherein said active substituted benzoic acid herbicidal agent is 3-amino-2,5-dichlorobenzoic acid.

12. A composition as set forth in claim 1 wherein a sufficient amount of the phosphate medium is present in the dry blended mixture to provide at least about 0.6 mole of the medium for each mole of active herbicidal agent in the initially dry blended mixture.

13. A composition as set forth in claim 1 wherein is included a mixture of said herbicidally active agents which are dry blended with the phosphate medium.

14. A composition as set forth in claim 1 wherein is included an anti-caking agent relatively uniformly distributed throughout in the dry blended mixture.

15. A dry, water-soluble substituted phenoxy and/or benzoic acid herbicide powder composition comprising;
    a dry blended mixture on a parts by weight basis of about
        31 parts of dry, solid powder particles of 2,4D,
        16 parts of dry, solid powder particles of MCPP,
        3 parts of dry, solid powder particles of dicamba, and
        40 parts of trisodium phosphate
    said 2,4-D, MCPP, dicamba and trisodium phosphate having been dry blended in powdered form without changing the physical state of the particles to retain the discrete particulate character thereof, and in the absence of chemical reaction between said 2,4-D, MCPP and dicamba with the trisodium phosphate or tripotassium phosphate to form a relatively uniform dry mixture thereof.

16. A dry, water-soluble substituted phenoxy and/or benzoic acid herbicide powder composition comprising;

a dry blended mixture on a parts by weight basis of about 37 parts of dry, solid powder particles of 2,4 D, 20 parts of dry, solid powder particles of MCPP, 4 parts of dry, solid powder particles of dicamba, and 30 parts of trisodium phosphate said 2,4-D, MCPP, dicamba and trisodium phosphate having been dry blended in powdered form without changing the physical state of the particles to retain the discrete particulate character thereof, and in the absence of chemical reaction between said 2,4-D, MCPP and dicamba with the trisodium phosphate to form a relatively uniform dry mixture thereof.

17. A dry, water-soluble substituted phenoxy and/or benzoic acid herbicide powder composition comprising;

a dry blended mixture on a parts by weight basis of about 31 parts of dry, solid powder particles of 2,4-D, 16 parts of dry, solid powder particles of MCPP, 3 parts of dry, solid powder particles of dicamba, and 40 parts of tripotassium phosphate said 2,4-D, MCPP, dicamba and tripotassium phosphate having been dry blended in powdered form without changing the physical state of the particles to retain the discrete particulate character thereof, and in the absence of chemical reaction between said 2,4-D, MCPP and dicamba with the tripotassium phosphate to form a relatively uniform dry mixture thereof.

18. A method of preparing a dry, water-soluble, substituted phenoxy and/or benzoic acid herbicide powder composition consisting essentially of the steps of:

providing a first quantity of dry, powder particles of a substantially solid herbicidal agent selected from the group consisting of herbicidally active phenoxy acids and substituted herbicidally active benzoic acids, which are not readily soluble in water;

providing a second quantity of dry, solid powder particles selected from the group consisting of trisodium phosphate and tripotassium phosphate as a solubilization medium for the herbicidal agent, said first and second quantities of the herbicidal agent and the solubilization medium being the predominate constituents of the composition, there being from 0.6 mole to about 1.15 mole of solubilization medium for each mole of herbicidal agent; and dry blending the herbicidal agent and the solubilization medium in powdered form without changing the physical state of the particles to retain the discrete particulate character of each of said first and second quantities of said particles, and in the absence of chemical reaction between said herbicidal agent and said solubilization medium to produce a relatively uniform dry mixture thereof, a sufficient quantity of the phosphate solubilization medium being provided in the dry blended mixture in relationship to the quantity of herbicidal agent combined therewith to cause the powdered dry blended mixture to substantially dissolve in water during preparation by the applicator of a herbicidal solution which contains an adequate proportion of the herbicidal agent to provide from about 0.1% to about 2½% by weight of the active herbicidal agent in the herbicidal solution.

19. A method as set forth in claim 18 wherein said dry solubilization medium is trisodium phosphate.

20. An herbicide as set forth in claim 18 wherein said dry solubilization medium is tripotassium phosphate.

* * * * *